United States Patent [19]

Fujiki et al.

[11] Patent Number: 5,591,028

[45] Date of Patent: Jan. 7, 1997

[54] DENTAL CUTTING TOOL HOLDER

[75] Inventors: Setsuo Fujiki; Shozo Nakayama; Haruo Ogawa; Makoto Numakawa; Minoru Hayashida; Suezo Inoue; Yasuhiro Higashida, all of Kyoto, Japan

[73] Assignee: J. Morita Manufacturing Corporation, Kyoto, Japan

[21] Appl. No.: 364,545

[22] Filed: Dec. 27, 1994

[30] Foreign Application Priority Data

Dec. 28, 1993 [JP] Japan .................................. 5-335264
Apr. 13, 1994 [JP] Japan .................................. 6-075134

[51] Int. Cl.⁶ ..................................................... A61C 1/14
[52] U.S. Cl. ..................................................... 433/129
[58] Field of Search ................................. 433/127, 128, 433/129, 132

[56] References Cited

U.S. PATENT DOCUMENTS

| | | | |
|---|---|---|---|
| 514,073 | 2/1894 | Hesse | 433/127 X |
| 713,826 | 11/1902 | Wilkens | 433/129 X |
| 3,488,850 | 1/1970 | Lieb et al. | 433/129 |
| 3,494,363 | 1/1970 | Peters | 433/129 X |
| 3,646,677 | 3/1972 | Saupe et al. | 433/127 |
| 3,672,060 | 6/1972 | Eibofner et al. | 433/127 |
| 4,279,597 | 7/1981 | Grimm | 433/129 |
| 5,011,408 | 4/1991 | Nakanishi | 433/127 |
| 5,090,906 | 2/1992 | Pernot | 433/127 |
| 5,402,580 | 4/1995 | Seto et al. | 30/394 |

FOREIGN PATENT DOCUMENTS

| | | |
|---|---|---|
| 0098754A1 | 1/1984 | European Pat. Off. .......... A61C 1/14 |
| 0420169A1 | 4/1991 | European Pat. Off. .......... A61C 1/14 |
| 56-151035 | 11/1981 | Japan . |
| 61-30650 | 9/1986 | Japan . |
| 3-53215 | 5/1991 | Japan . |

*Primary Examiner*—Robert P. Swiatek
*Assistant Examiner*—Yvonne R. Abbott
*Attorney, Agent, or Firm*—Koda and Androlia

[57] ABSTRACT

A dental cutting tool holder which prevents the occurrence of sliding between the cutting tool and collet chuck at high-speed rotation, and prevents dislocation of the cutting tool securely, comprising a collet chuck into which a dental cutting tool is inserted detachably, and which comprises a right cylindrical section and a plurality of arc-section segments which are contiguous to the cylindrical section and divided in a circumferential direction; a rotor into which the collet chuck is inserted, and which is driven for rotation around the axis of rotation together with the collet chuck; and a clamping member which intervenes between the collet chuck and the rotor to press the respective segments inward in a radial direction by its displacement toward one end of the axis relative to the collet chuck while releasing the inward, radially pressed condition by its displacement toward the other end of the axis. The respective segments are formed with recess sections and an axially extending protrusion section.

5 Claims, 15 Drawing Sheets

DENTAL CUTTING TOOL HOLDER

BACKGROUND OF THE INVENTION

1. Field of the Invention

The present invention relates to a dental cutting tool holder for detachably installing a dental cutting tool which is used for cutting hard tissues including teeth, dentary, etc., in the head of a handpiece.

2. Description of the Related Art

Indispensable for dental care are cutting operations for teeth aiming at preparing cavities, forming abutment teeth, cutting off carious sites, enlarging root canals, etc., and instruments used for such cutting operations include, for example, air turbine handpieces. This type of cutting tool is detachably installed in the head of a handpiece and driven for rotation at a high speed on the order of 400–500 thousand rpm. Therefore, in order to prevent the dislocation of the cutting tool in the oral cavity of the patient under care, it is necessary that the cutting tool be securely held in the head of the handpiece. In addition, since a variety of types of cutting tools are used appropriately depending on the shape of the cavity, the cutting site, etc., preferably they are installed in the head of a handpiece in a readily detachable manner.

Representative of the prior art is, for example, the one described in Japanese Unexamined Utility Model Publication JP-U 60-27908 (Japanese Examined Utility Model Publication JP-Y2 61-30650). According to this device of the prior art, a chuck member, a counterpart of the collet chuck according to the present invention, in the head for receiving a cutting tool is provided with a plurality of chuck bits, and when the chuck member is displaced in one axial direction upon insertion of the cutting tool, the chuck member is pressed against the tapered inner circumference of the inserted spindle while the outer circumferences of the chuck bits are pressed inward in a radial direction, thereby providing a structure which allows the inner circumferences of the inward displaced chuck bits to press against the outer circumference of the cutting tool to hold the cutting tool.

This device of the prior art, however, produces ununiform pressure from the respective chuck members on the cutting tool because of the dimensional variabilities of the respective chuck bits due to discrete structures of the chuck bits and the chuck member. Consequently, the axis of the spindle does not match the axis of the cutting tool, resulting in creation of vibrations during cutting which may cause the patient pain while cutting the tooth. Furthermore, since the vibrations make a noise which tends to provoke fear and anxiety in patients, there is presented a problem of increased emotional upset.

Another embodiment of the prior art is described in, for example, Japanese Examined Utility Model Publication JP-U 3-53215. According to this prior art, there is formed a notched stepped section on the inner circumference of collet, corresponding to the collet chuck according to the present invention, in order to provide a structure which allows the corner section of the notched stepped section to engage in the outer circumference of the cutting tool by the chucking action, thereby preventing the cutting tool from being dislocated, even if force is exerted on the inserted cutting tool to facilitate its dislocation.

This device of the prior art, however, has a drawback in that even with great axial frictional force of the notched stepped section exerted on the cutting tool, the cutting tool slides in the direction of rotation during cutting due to extremely poor frictional force in the direction of rotation, eventually allowing the cutting tool to readily work down in spite of great clamping force applied on the cutting tool.

A further prior art is disclosed in, e.g., Japanese Unexamined Patent Publication JP-U 56-151035. This device of the prior art provides, as is shown in FIG. 15, a structure with a manipulation member 221 comprising a press cap with a recess 222 in the center. The inner bottom surface 223 of the recess 222 is plane, and due to the small contact area of the press cap and the finger, the finger must press harder. A much greater force must be applied in cases where the size of the finger does not fit the size of the recess 222. This additional requirement results in a heavy burden imposed on dentists who treat many patients daily, because the manipulation member must be used several times for each patient to change dental cutting tools.

SUMMARY OF THE INVENTION

Accordingly, an object of the present invention is to provide a dental cutting tool holder which may securely prevent the occurrence of vibrations and dislocation of the cutting tool during cutting and lightens the burden imposed on the finger of the dentist when changing cutting tools.

The present invention relates to a dental cutting tool holder comprising:

a collet chuck into which a dental cutting tool is inserted detachably, and comprises a right cylindrical section and a plurality of arc-section segments which are contiguous to the cylindrical section and divided in a circumferential direction;

a rotor into which the collet chuck is inserted, and which is driven for rotation around the axis of rotation together with the collet chuck; and a clamping member which intervenes between the collet chuck and the rotor to press the respective segments inward in a radial direction by the displacement thereof toward one axial end relative to the collet chuck while releasing the inward, radially pressed condition by the displacement thereof toward the other axial end, wherein the respective segments are formed with a recess section located back from the outer circumference of the inserted cutting tool outward in a radial direction, and an axial protrusion section jutting out inward in a radial direction from the inner circumference of the recess section.

The present invention is further characterized in that the respective protrusion sections form the respective segments at their upstream ends in the direction of rotation of the rotor.

Another characteristic aspect of the present invention resides in that each protrusion section is provided with a plurality of notches spaced apart along the axis of the collet chuck.

The present invention also relates to a dental cutting tool holder with a structure whereby a manipulation member provided in the head housing of a handpiece for detachably holding a dental cutting tool therein is pressed with the finger along the axis of the dental cutting tool so that the denial cutting tool is released, characterized in that the pushing surface of the manipulation member is curvedly formed into a concave.

The present invention is still further characterized in that the entire pushing surface of the manipulation member is curvedly formed into a concave with a 25–35 mm radius of curvature.

The present invention further relates to a dental cutting tool holder characterized by comprising:

a collet chuck into which a dental cutting tool is inserted detachably, and which comprises a right cylindrical section and a plurality of arc-section segments which are contiguous to the cylindrical section and divided in a circumferential direction;

a rotor into which the collet chuck is inserted, and is driven for rotation around the axis of rotation together with the collet chuck;

a clamping member which intervenes between the collet chuck and the rotor to press the respective segments inward in a radial direction by its displacement toward one axial end relative to the collet chuck while releasing the inward, radially pressed condition by its displacement toward the other axial end;

a hollow cylindrical head housing for receiving the collet chuck, rotor and clamping member; and a manipulation member which is provided at the other axial end of the head housing and releases the dental cutting tool upon axial pressing with the finger, wherein the pushing surface of the manipulation member is curvedly formed into a concave.

A still further characteristic aspect of the present invention resides in the head housing formed with first and second annular recess grooves which are open to the facing internal space and communicated with each other, and a jet provided in either of the first and second annular recess grooves positioned closer to the bottom of the head housing, which inclines inward in a radial direction toward the tip of the cutting tool, and injects first and second fluids which are separately supplied to the first and second annular recess grooves, or a mixture thereof.

According to the present invention, the cylindrical section of the collet chuck is formed with a plurality of successive segments, each segment comprising a recess section located back from the outer circumference of the cutting tool inserted in the collet chuck, outward in a radial direction, and a protrusion section jutting out from the recess section inward in a radial direction. This type collet chuck is inserted into the rotor, and driven for rotation together with the rotor. The clamping member is situated between the rotor and the collect chuck. By the displacement of the clamping member toward one axial end the respective holding segments are pressed inward in a radial direction. On the other hand, the displacement of the clamping member toward the other axial end allows the segments to be released from the inward, radially pressed condition.

As mentioned above, the displacement of the clamping member toward either of the axial ends allows the respective protrusion sections to press the inserted cutting tool, or the cutting tool to be released from the pressed condition, thus keeping it held in a detachable manner. In addition, since the respective protrusions extend axially, great friction may be applied to the inserted cutting tool both axially and circumferentially, which friction serves to consistently prevent the dislocation of the cutting tool during cutting. Furthermore, since each protrusion is formed integrally with each counterpart segment the dimensional error may be minimized more easily than according to the prior art, thereby enabling the cutting tool to be held by uniform pushing pressures from the respective protrusions applied to its outer circumference. Accordingly, the matching between the axis of the collet chuck and the axis of the cutting tool may be accomplished with high accuracy, to prevent the occurrence of vibrations and noises.

Also according to the present invention, since all the protrusion sections are formed at the upstream ends in the direction of rotation of the rotor, during rotation the pushing pressure applied to the downstream corner section of each protrusion section in the direction of rotation is held higher than the pushing pressure applied to the upstream corner section of each counterpart protrusion section in the direction of rotation, for which reason the sliding of the collet chuck and the cutting tool during rotation in the direction of rotation, is consistently prevented, and thus the reliability of preventing dislocation of the cutting tool may be increased markedly.

Also according to the present invention, since a plurality of axially spaced notches are formed in each protrusion section, fretting between the inner circumference of each protrusion section and the outer circumference of the cutting tool may be minimized, and this minimization naturally leads to a minimum creation of smooth surfaces, thereby consistently preventing the occurrence of sliding of the cutting tool with respect to the collet chuck during rotation.

Also according to the present invention, the entire pushing surface of the manipulation member is curvedly formed into a concave, preferably a concave with a 25–35 mm radius of curvature, and thus the area of its contact with the finger may be maximized regardless of the size of the finger, resulting in a lightened burden for the dentist when changing cutting tools.

Also according to the present invention, first and second annular grooves which communicate with each other are provided in the head housing, and a first fluid (compressed air) and a second fluid (water) are appropriately supplied thereto to cool the site subjected to cutting.

As mentioned above, the present invention allows the inserted cutting tool to be held by the protrusion formed axially on each segment of the collet chuck, making it possible to securely hold the cutting tool due to the elimination of sliding between the collet chuck and the cutting tool both axially and in the direction of rotation.

Also according to the present invention, the respective protrusion sections are formed at the upstream ends in the direction of rotation, and therefore the sliding of the collet chuck and the cutting tool during rotation, in the direction of rotation, is more surely prevented, and the reliability of preventing dislocation of the cutting tool during cutting is improved.

Furthermore, according to the present invention, since a plurality of notches are formed in each protrusion section at intervals along the axis of the collet chuck, the area of contact between each protrusion and the cutting tool may be minimized to prevent fretting between the outer circumference of the cutting tool and the inner circumference of each protrusion section, and the contact surface of each protrusion section except for the notches serves to place a great localized stress on the cutting tool to prevent the sliding and thus to ensure no dislocation of the cutting tool during rotation.

Also according to the present invention, since the manipulation member provided in the head housing is formed with a pushing surface formed curvedly into a concave, the burden of manipulating the pushing surface with the finger to release the cutting tool may be lightened.

The present invention also allows the heat of cutting due to cutting of teeth, etc. to be easily reduced by the first and second annular grooves for receiving the first and second fluids in admixture, and the jet, all positioned in the head housing.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Figure 1:
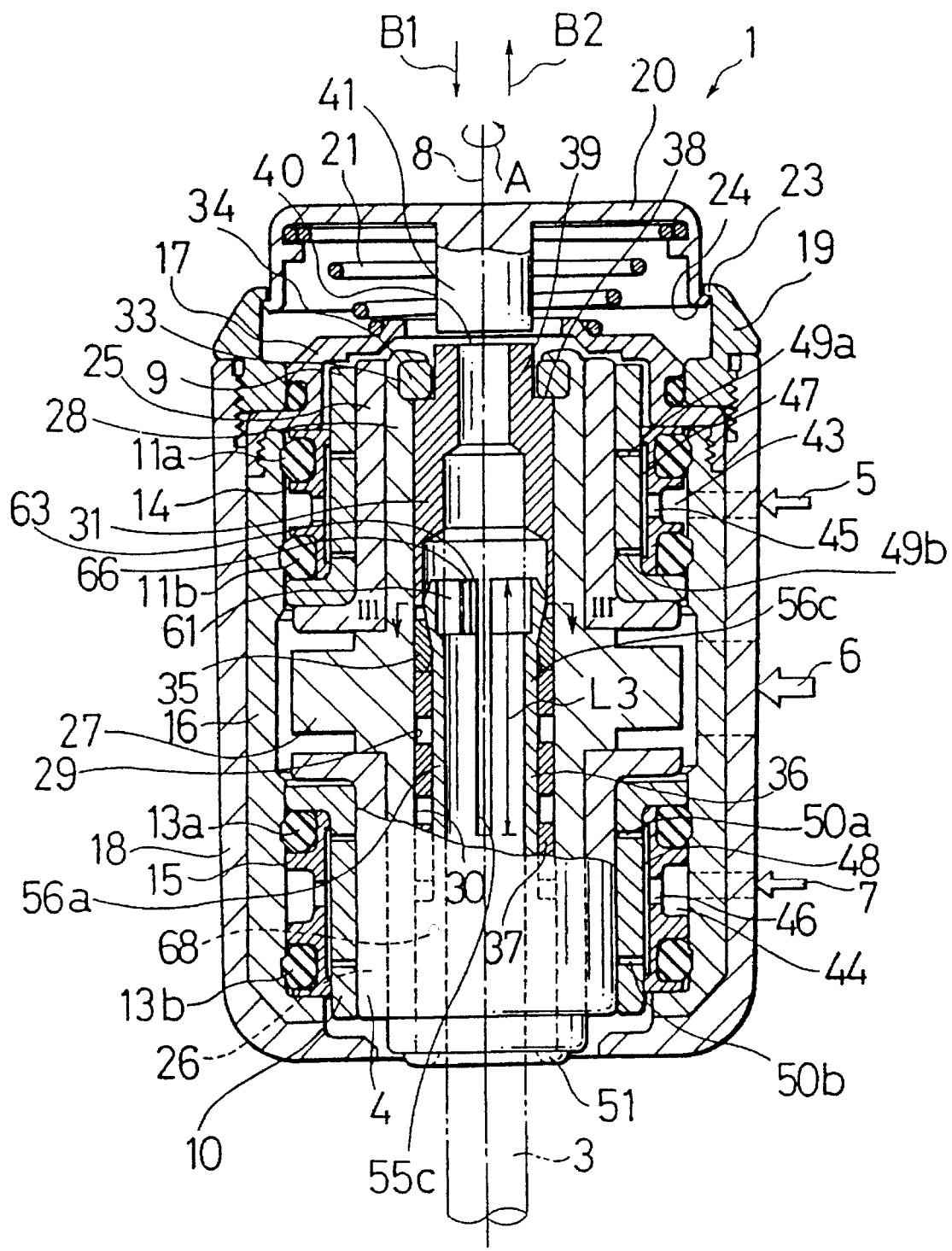
FIG. 1 is a sectional view showing the inner structure of the head 1 of an air turbine handpiece according to an embodiment of the present invention.

Now referring to the drawings, preferred embodiments of the invention are described below.

FIG. 1 is a sectional view showing the inner structure of the head 1 of an air turbine handpiece according to an embodiment of the present invention. The head 1 of an dental air turbine handpiece receives therein a rotor 4 into which a cutting tool 3 for cutting teeth, dentary, etc., such as a bur, is installed detachably, and this rotor 4 is driven for rotation at a high speed around the axis of rotation 8 in the direction indicated by the arrow A, by compressed air 5, 6 and 7 supplied via piping (not shown) provided in the grip section contiguous to the head 1. The speed of rotation may be set at approximately 400–500 thousand rpm for the so-called high speed cutting, or may be on the order of 10–20 thousand rpm for low speed cutting. The cutting tool 3 may be made of a hard-wearing material, including, e.g., carbon steel, carbide, etc.

Over the rotor 4 are coaxially fitted a pair of upper and lower annular metal bearing members 9 and 10, and seal bearing members 14 and 15 over which pairs of O-rings 11a, 11b; and 13a, 13b are fitted, are mounted on the respective bearing members 14 and 15. The respective O-rings 11a, 11b; and 13a, 13b elastically contact with the entire inner circumference of a roughly right cylindrical liner 16 all along the circumference to accomplish air tightness.

Threadedly engaged with the liner 16 is a liner cap 17, and the liner 16 and the liner cap 17 are received in a bottomed cylinder-like metal head housing 18. The head housing 18 is engaged threadedly with a dislocation-preventive annular cover 19. Mounted in this cover 19 is an manipulation member 20 in a free displacement manner in the direction of the arrows B1 and B2, with a conical compression coiled spring 21 intervening between the manipulation member 20 and the liner cap 17. The cover 19 is provided with an inward projection 23 formed along the entire circumference, whereas an outward projection 24 jutting outward in a radial direction is formed along the entire circumference of the manipulation member 20. The outward projection 24 is engaged with the inward projection 23 contacting therewith, with the manipulation member 20 elastically biased by the compression coiled spring 21 in the opposite direction from the liner cap 17 (in the direction indicated by the arrow B2). By pressing the manipulation member 20 in the direction indicated by the arrow B1 against the spring force of the compression coiled spring 21, the cutting tool 3 may be extracted from the head 1, whereas the cutting tool 3 is held by releasing the manipulation member 20 from the condition pressed in the direction indicated by the arrow B1, to displace the manipulation member 20 in the direction indicated by the arrow B2 by the spring force of the compression coiled spring 21.

The rotor 4 comprises a pair of upper and lower metal sleeves 25 and 26 which are mounted at a distance of about 10 μm from the inner circumferences of the respective bearing members 9 and 10; a rotor 28 provided with the respective sleeves 25 and 26 mounted thereon, and further provided with an integral assembly of a plurality of blades 27 around the center in the direction of the axis 8; a working shaft 31 inserted into the central opening 30 surrounded by the right cylindrical inner circumference 29 of the rotor 28, in a free displacement manner along the axis 8; a stopper 34 fitted in an annular recess groove 33 formed at one axial end of the rotor 28; an annular clamping member 35 which is inserted into the central opening 30 coaxially with the working shaft 31; a collet chuck 36 on which the clamping member 35 is mounted; and a compression coiled spring 37 which is mounted on the collet chuck 36 to bias the clamping member 35 elastically in the direction indicated by the arrow B2.

At one axial end of the working shaft 31 is formed an annular contact surface 38 which extends in an imaginary plane perpendicular to the axis 8, and the stopper 34 in contact with the contact surface 38 prevents the displacement in the direction indicated by the arrow B2. The working shaft 31 is further provided with a right cylindrical, smaller diameter section 39 formed integrated therewith which juts from the stopper 34 while being in contact with the contact surface 38, and an edge face 40 thereof is pressed upon contact with the right cylindrical pushing projection 41 of the manipulation member 20, thereby allowing the working shaft 31 to be displaced in the direction indicated by the arrow B1 for displacement of the clamping member 35 against the spring force of the compression coiled spring 37, and eventually making it possible to extract the cutting tool 3 therefrom.

The rotor 28 is driven for rotation by the compressed air 6, and this rotation drives the whole rotor 4 to rotate. On the other hand, the compressed air 5 and 7 is supplied into annular spaces 43 and 44 formed between the respective O-rings 11a, 11b; and 13a, 13b, and introduced, via a plurality of spaced transparent openings 45 and 46 formed circumferentially in the respective seal bearing members 14 and 15, into annular spaces 47 and 48 which face the respective seal bearing members 14 and 15, and recessed in the inner circumferences of the respective bearing members 9 and 10, and then supplied, via a plurality of spaced supply openings 49a, 49b; and 50a, 50b formed along the circumferences of the bearing members 9 and 10, into the minute space formed between the respective inner circumferences of the respective bearing members 9 and 10 and the outer circumferences of the sleeves 25 and 26, after which the air is discharged outside, and thus the rotor 4 is driven for rotation at a high speed of approximately 400–500 rpm without contact with the respective bearing members 9 and 10.

The compression coiled spring 37 has a spring force on the order of 2–4 kg per piece. Further, the cutting tool 3 has a outer diameter φ of 1.590–1.600 mm according to the ISO standard, while the tolerance between the inner diameter of the central opening 30 and the outer diameter 3 is on the order of 12–13 μm at the maximum, and the tip is prevented from dislocation by a bending section 51.

Figure 2:
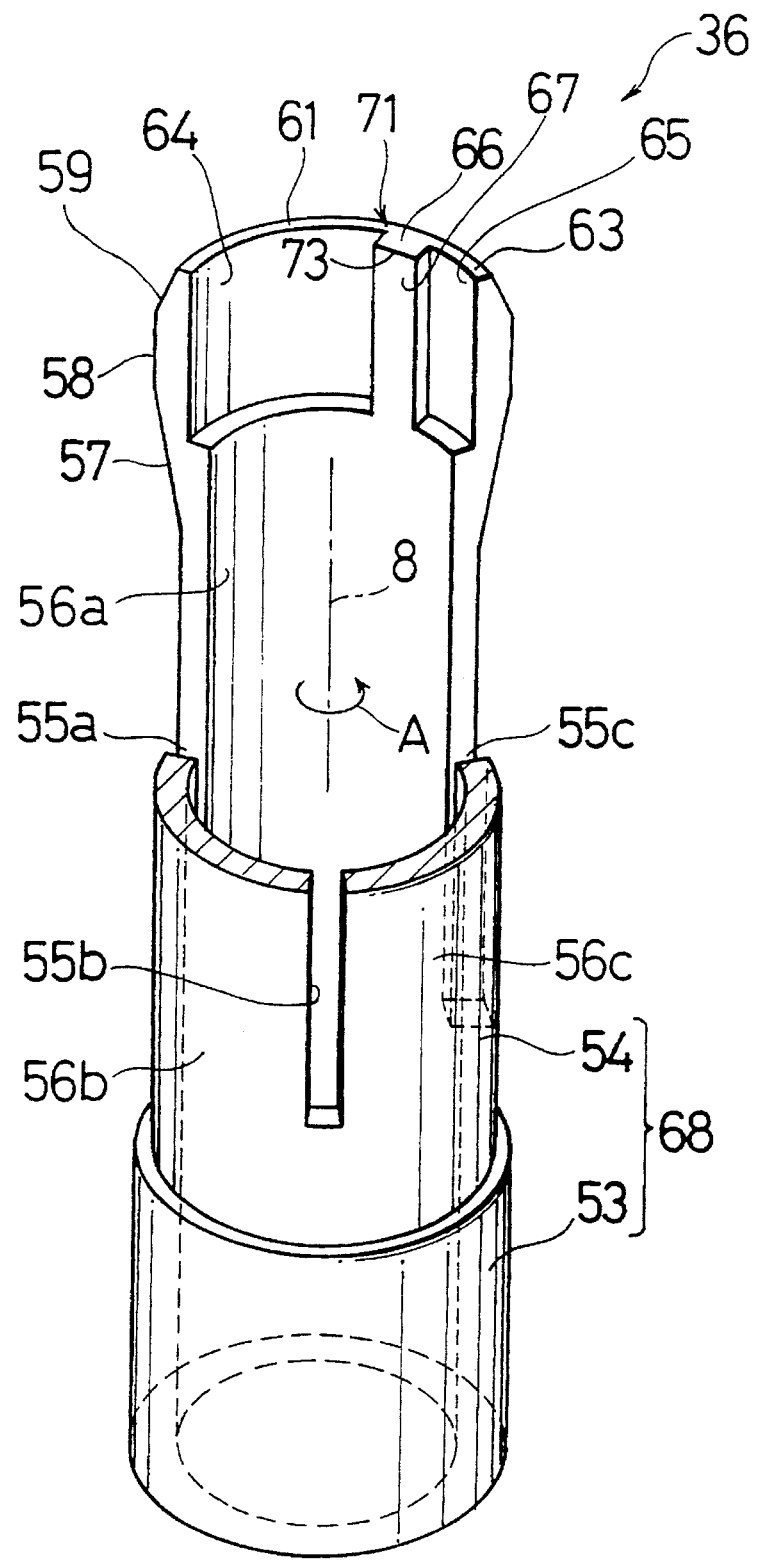
FIG. 2 is a partially cutaway view in perspective of a collet chuck 36.

FIG. 2 is a partially cutaway view in perspective of the collet chuck 36. The collet chuck 36 comprises a right cylindrical, larger diameter section 53 made of a harder material than the cutting tool 3, e.g., a high-speed tool steel; a smaller diameter section 54 contiguous to the larger diameter section 53 via a step surface 54; and a plurality (three according to the present embodiment) of arc- section segments 56a, 56b and 56c spaced at identical distances circumferentially by dividing grooves 55a, 55b and 55c which are contiguous to the smaller diameter section 54, and are formed every 120° along the circumference.

The respective segments 56a–56c comprise a first guide surface 57 in the form of a truncated cone, a second guide surface 58 in the form of a right cylinder, and a third guide surface 59 which tapers toward the free ends, all formed along the inner circumferences of the respective free ends.

Figure 3:
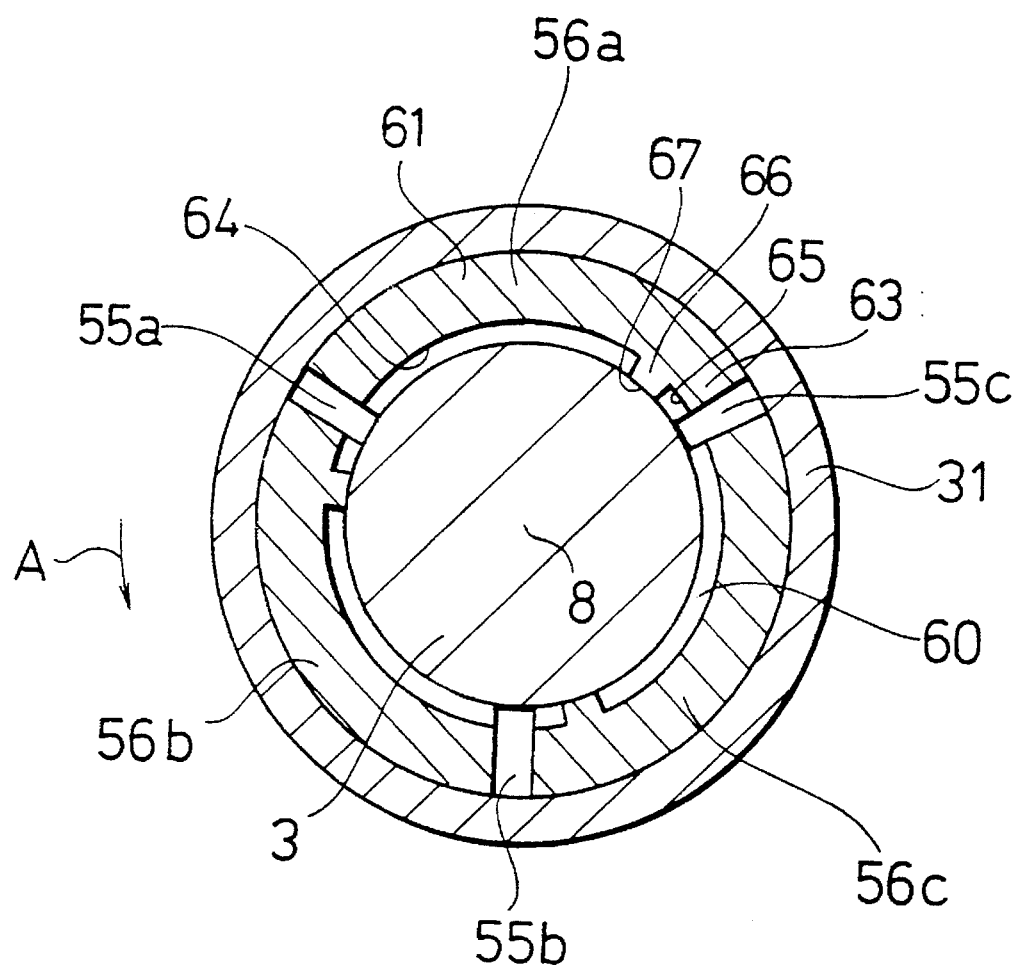
FIG. 3 is an enlarged sectional view taken on the cutting-plane line III—III of FIG. 1.

FIG. 3 is an enlarged sectional view taken on the cutting-plane line III—III of FIG. 1. With reference to FIG. 2 as well, formed on the inner circumferences of the respective free ends of the respective segments 56a–56c are first and second recess sections 61 and 63 which are located back from the outer circumference 60 of the inserted cutting tool 3, outward in a radial direction, and a protrusion section 66 which juts out from the respective inner circumferences 64 and 65 of the first and second recess sections 61 and 63, inward in a radial direction, and extends along the direction of the axis 8.

Each protrusion section 66 is formed at the upstream end in the direction of rotation A of the rotor 4, and the arc-section inner surface 67 of each protrusion section 66 is in surface contact with the outer circumference 60 of the cutting tool 3, whereas the respective inner circumferences 64 and 65 of the first and second recess sections 61 and 63 are spaced apart from the outer circumference 60. The larger diameter section 53 and the smaller diameter section 54 compose a cylindrical section 68.

As a summary of the structure mentioned above, the holder according to the present embodiment may be concluded to have the structure described below. That is, the holder comprises a collet chuck 36 into which a dental cutting tool 3 is inserted detachably, and which comprises a right cylindrical section 68 and a plurality of arc-section segments 56a, 56b and 56c which are contiguous to the cylindrical section 68 and divided in a circumferential direction; a rotor 4 into which the collet chuck 36 is inserted, and which is driven for rotation around the axis of rotation 8 together with the collet chuck 36; and a clamping member 35 which intervenes between the collet chuck 36 and the rotor 4 to press the respective segments 56a, 56b and 56c inward in a radial direction by its displacement toward one end of the axis 8 while releasing the inward, radially pressed condition by its displacement toward the other end of the axis 8. The respective segments 56a, 56b and 56c are formed with first and second recess sections 61 and 63 located back from the outer circumference 60 of the inserted cutting tool 3 outward in a radial direction, and with a protrusion section 66 which juts inward in a radial direction from the inner circumferences 64 and 65 of the recess sections 61 and 63, and extends in the direction of the axis 8, with the respective protrusion sections 66 forming the respective segments 56a, 56b and 56c at their upstream ends in the direction of rotation A of the rotor 4.

Figure 4A:
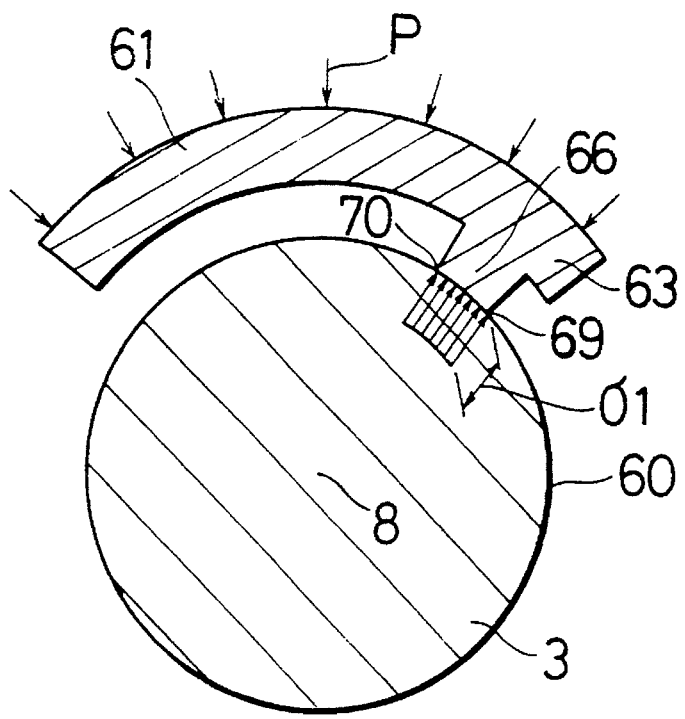
FIGS. 4A, 4B are illustrative views explaining the condition of a cutting tool 3 pressed by the protrusion section 66 of a collet chuck 36.
Figure 4B:
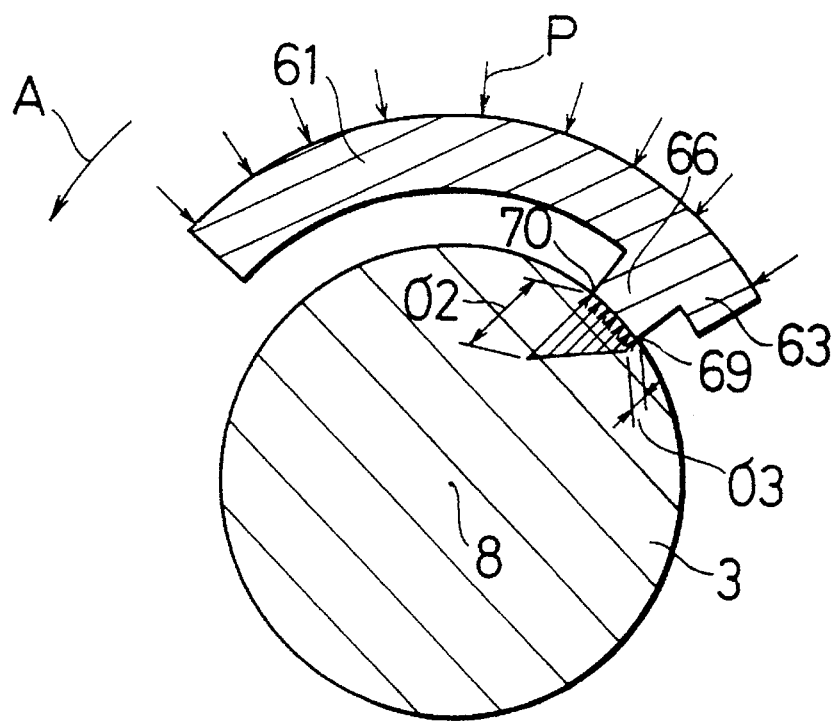

With this structure, as is shown in FIG. 4(1), while the rotor 4 is not driven for rotation, the respective segments 56a–56c circumferentially receive even pushing pressure P from the clamping member 35 inward in a radial direction, whereas the pushing pressure applied to the cutting tool 3 from the respective protrusion sections 66 produces an almost even compression stress σ1 all the surface from the upstream end 69 to the downstream end 70 in the direction of rotation A.

Next, as is shown in FIG. 4(2), once the rotor 4 starts to rotate at a high speed on the order of 400–500 thousand rpm in the direction of rotation A, the compression stress σ2 pressed on the cutting tool 3 becomes much greater at the downstream corner section 70 in the direction of rotation A of each protrusion section 66 than the compression stress σ3 at the upstream corner section 69, and as a result the downward corner section 70 of each protrusion section 66 is, so to speak, engaged in the cutting tool 3, thereby allowing the cutting tool 3 to resist with a large friction against the torque in the direction of rotation indicated by the arrow A which is exerted on the cutting tool 3 from each protrusion section 66.

Moreover, since each protrusion section 66 is formed lengthwise along the axis 8, a great contact length or contact area is provided in the direction perpendicular to the direction of rotation A, and thus there is no possibility of sliding in the direction of rotation A. On the other hand, regarding sliding in the direction of the axis 8, the corner section 73 at which the edge face 71 (see FIG. 2) of each protrusion section 66 and the inner circumference 67 cross each other is pressed against the outer circumference 60 of the cutting tool 3, and this pressing also contributes to the prevention of sliding in the direction of the axis 8.

In addition, since the respective protrusion sections 66 are formed integrally with the respective counterpart segments 56a–56c, unlike the case where they are formed separately as discussed above in relation to the prior art, dimensional errors may be minimized, and thus it is possible to match the central axis of the inserted cutting tool 3 to the axis of rotation. Accordingly, there is no risk of causing vibrations even when driven at high-speed rotation, and thus stable high-speed rotation may be achieved. Furthermore, since the respective segments 56a–56c are formed longer than the cylindrical section 68, even when the respective segments 56a–56c are pressed inward by the clamping member 35, there is no possibility of inward, radial deflection at a great angle from the axis 8, and therefore it is possible to prevent weakening, and consequently breakage, of the respective segments 56a–56c.

Figure 5:
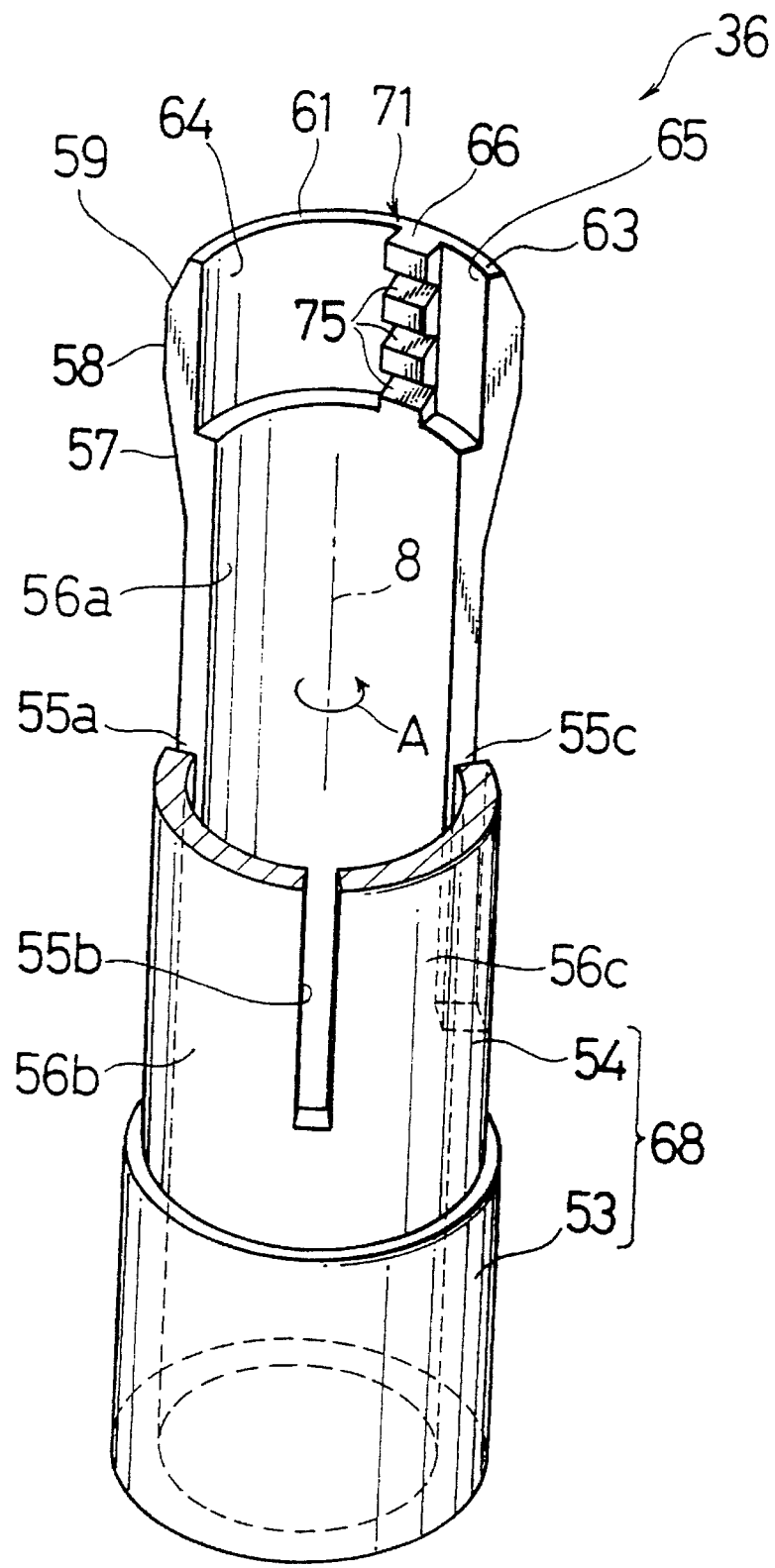
FIG. 5 is a partially cutaway view in perspective of a collet chuck 36 according to another embodiment of the present invention.

According to another embodiment of the present invention, as is shown in FIG. 5, each protrusion section 66 may be formed with a plurality (three in this embodiment) of notches 75 spaced apart in the direction of the axis 8 of the collet chuck 36. With the notches 75 formed in this manner, as is shown enlarged in FIG. 6, the contact areas between the respective protrusion sections 66 and the outer circumference 60 of the cutting tool 3 may be decreased as indicated by the reference symbols a1, a2 and a3 while increasing the contact pressures on the respective contact surfaces a1, a2 and a3 to prevent sliding of the cutting tool 3 and the collet chuck 36 in the direction of the axis 8 and in the direction of rotation A, thereby preventing the occurrence of fretting of the respective contact surfaces a1, a2 and a3. Incidentally, like elements are designated by like reference symbols used for the embodiment discussed above.

Figure 7:
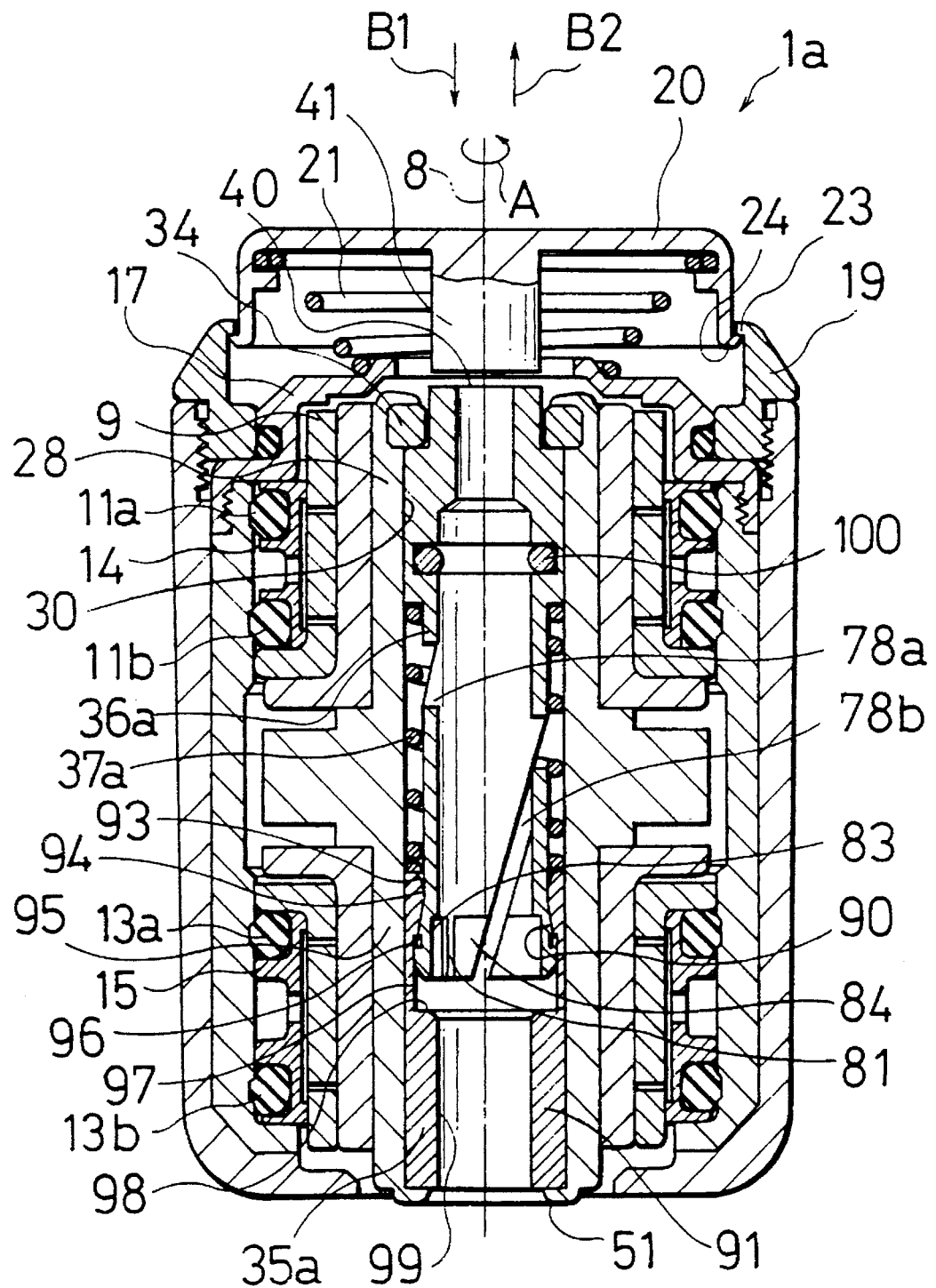
FIG. 7 is a sectional view showing the inner structure of the head 1a of an air turbine handpiece according to another embodiment of the present invention.
Figure 8:
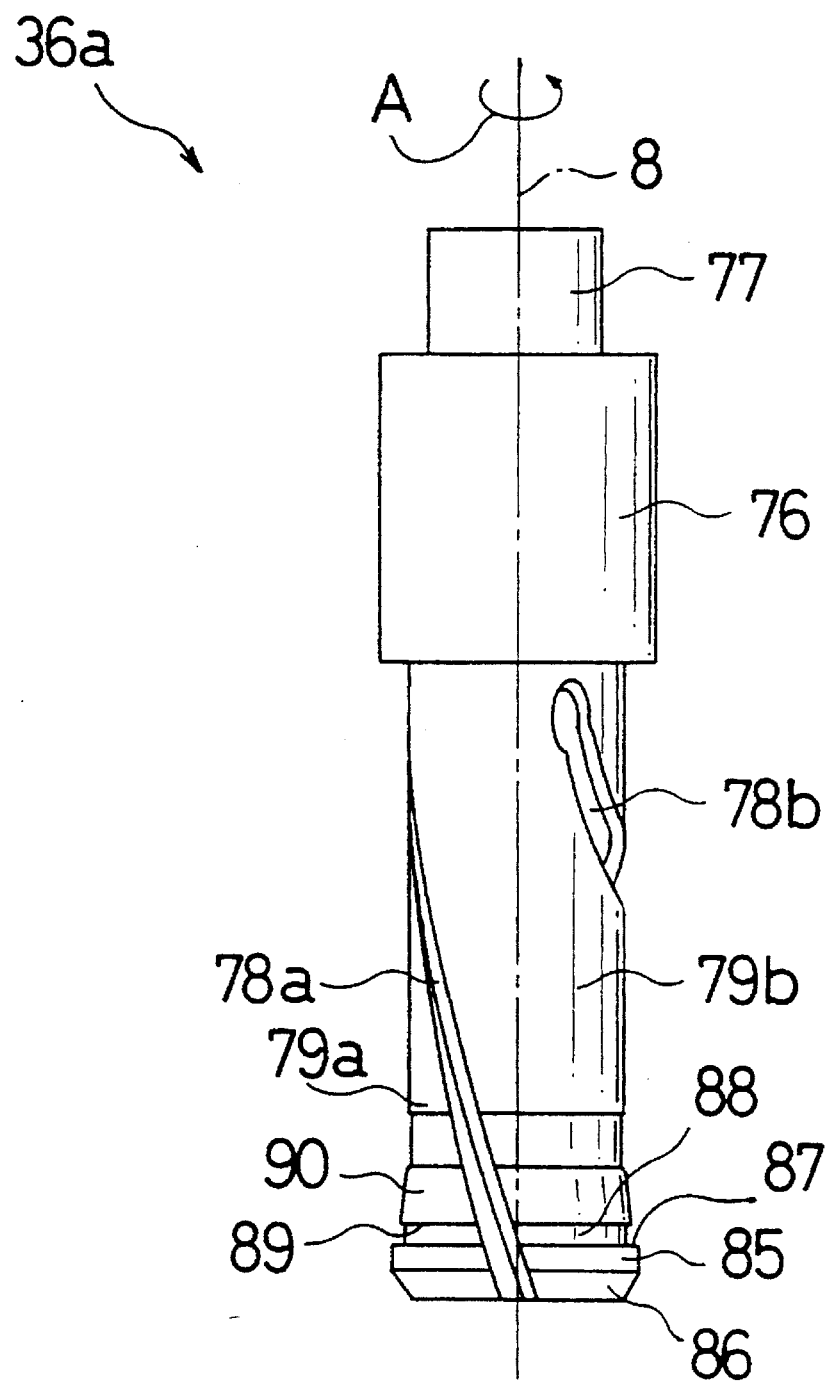
FIG. 8 is a front view of a collet chuck 36a built into the head 1a shown in FIG. 7.

FIG. 7 is a sectional view showing the inner structure of the head 1a of an air turbine handpiece according to another embodiment of the present invention; while FIG. 8 is a view of a collect chuck 36a built into the head 1a shown in FIG. 7.

In these embodiments the same reference symbols are designated for elements that correspond to those in the foregoing embodiments. In this embodiment, the central opening 30 of the rotor 28 receives the collet chuck 36a in such a manner that the chuck may be displaced along the axis 8 in the directions indicated by the arrows B1 and B2. This collet chuck 36a is elastically biased in the direction indicated by the arrow B2 by a compression coiled spring 37a supported by a clamping member 35a, to contact with a stopper 34, and in this condition displacement to the manipulation member 20 is prevented.

The collet chuck 36a comprises a right cylindrical section 76; a pushing section 77 which is contiguous to one axial end of the cylindrical section 76 and has a smaller diameter than the cylindrical section 76; and segments 79a and 79b which are contiguous to the other axial end of the cylindrical section 76, have a smaller diameter than the cylindrical section 76, and are separated by a plurality (two in this embodiment) of spiral dividing grooves 78a and 78b. On the inner circumference of the free end of each of the segments 79a and 79b at the downstream end in the direction of rotation A is formed a protrusion section 81, and downstream from the protrusion section 81 in the direction of rotation A is formed a first recess section 83, whereas a second recess section 84 is formed upstream in the direction of rotation A to the protrusion section 81.

On the other hand, on the outer circumference of the free end of each of the segments 79a and 79b there are formed a right cylindrical first guide surface 85; a truncated cone-like second guide surface 86 which tapers in the direction from the first guide surface 85 to the free end; a step face 87 located perpendicular to the circumference at the proximal end of the first guide surface 85; a right cylindrical, third guide surface 88 which has a smaller diameter than the first guide surface 85; a step face 89 which extends outward in a radial direction from and perpendicular to the circumference at the proximal end of the third guide surface 88, and faces the step face 87; and a truncated cone-like, fourth guide surface 90 which is contiguous to the outer circumference of the step face 89, and tapers toward the proximal end.

The clamping member 35a comprises a right cylindrical outer circumference 91, and from the proximal end to the other end on its inner circumference there are formed a truncated cone-like first inner circumference 93, a right cylindrical second inner circumference 94, a truncated cone-like, third inner circumference 95, a receiving face 96 extending rectangular to the axis, a right cylindrical, fourth inner circumference 97, a contact surface 98 extending rectangular to the axis, and a right cylindrical, fifth inner circumference 99 in that order.

When the cutting tool 3 is inserted in the collet chuck 36a, a sealant 100 elastically contacts with the outer circumference 60 of the cutting tool 3 to accomplish air tightness, and the fourth guide surface 90 of the collet chuck 36a is pressed inward in a radial direction by the third inner circumference 95 of the clamping member 35a, thus allowing the outer circumference 60 of the cutting tool 3 to be held by the protrusion section 81 with great strength. In an attempt to extract the cutting tool 3, when the manipulation member 20 is pressed in the direction indicated by the arrow B1, the collet chuck 36a is pressed down in the same direction (downward in FIG. 7) against the spring force of the compression coiled spring 37a, the respective segments 79a and 79b widen outward in a radial direction as the fourth guide surface 90 moves along the third inner circumference 95, and the respective protrusion sections 81 are estranged from the outer circumference 60 of the cutting tool 3, and the cutting tool 3 is released from its held state to promote its extraction from the head 1a.

Figure 6:
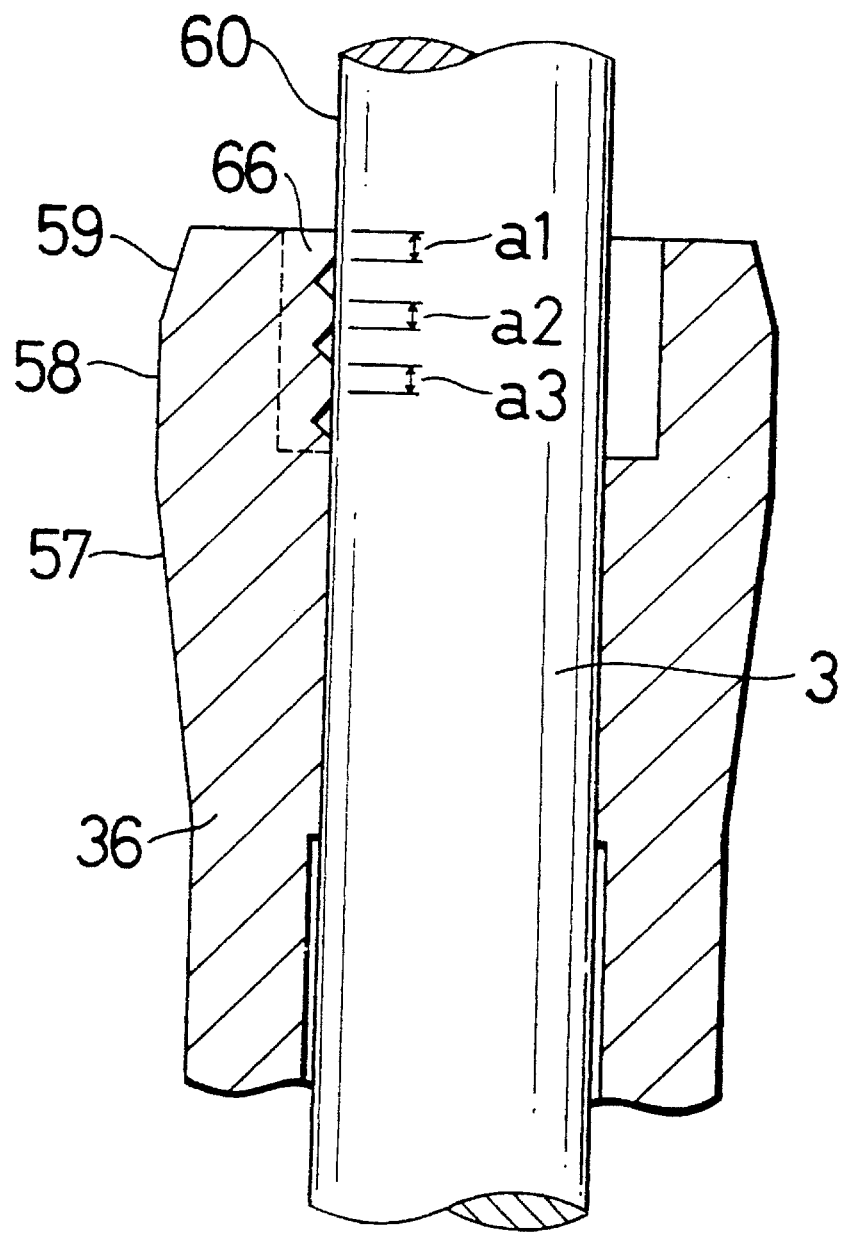
FIG. 6 is an enlarged sectional view showing the neighborhood of the protrusion section 66 of the collet chuck 36 shown in FIG. 5.

Also regarding the collet chuck 36a operated in this manner, the respective protrusion sections 81 may be provided with a plurality of notches 75 as shown in FIG. 5 and FIG. 6 referred to above.

Figure 9:
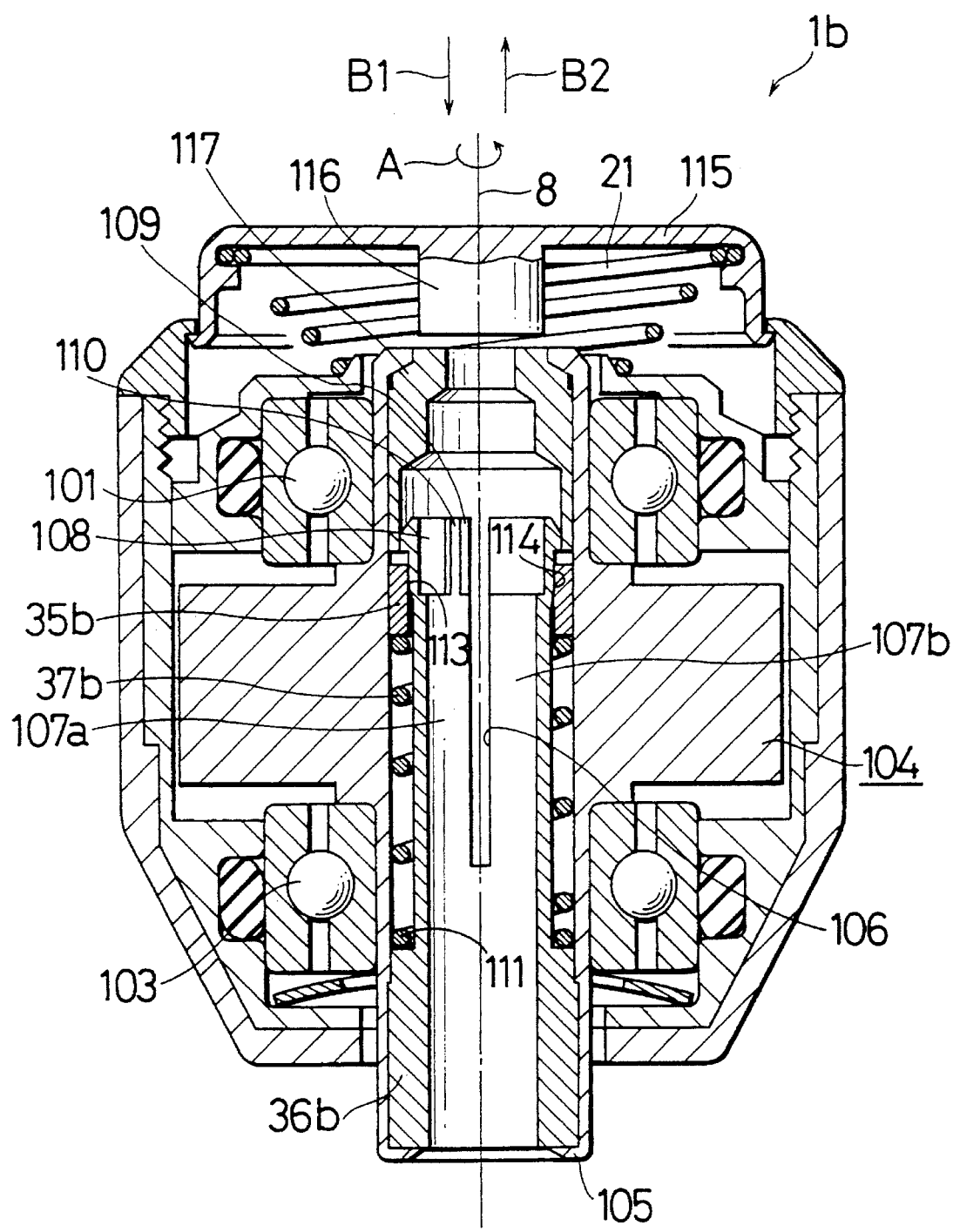
FIG. 9 is a sectional view showing the inner structure of the head 1b of a contra-angle handpiece according to another embodiment of the present invention.

FIG. 9 is a sectional view showing the internal structure of the contra-angle handpiece 1b according to another embodiment of the present invention. In the head 1b of the contra-angle handpiece is mounted a rotor 104 pivoted on a pair of upper and lower ball bearings 101 and 103, and in this rotor 104 is inserted a collet chuck 36b which is prevented from dislocation by a bending section 105. In the same manner as in the embodiment mentioned above, this collect chuck 36b is formed with segments 107a and 107b separated by a plurality of dividing grooves 106, and first and second recess sections 108 and 109 and a protrusion section 110 are formed at the free ends of the respective segments 107a and 107b.

The collet chuck 36b is mounted with a compression coiled spring 37b and a clamping member 35b, one end of the compression coiled spring 37b is supported by a spring bearing surface 111 of the collet chuck 36b, and the other end of the compression coiled spring 37b elastically presses the clamping member 35b. This clamping member 35 is formed with a truncated cone-like inner circumference 113, and this inner circumference 113 presses the truncated cone-like pushing surface 114 formed at the free end of each of the segments 107a and 107b of the collect chuck 36b to displace the respective segments 107a and 107b inward in a radial direction, thereby allowing the outer circumference of the cutting tool 3 to be held by the respective protrusion sections 110 with great strength.

In an attempt to extract the cutting tool 3 held in this manner, upon subjecting the manipulation member 115 to pressing operation in the direction of the arrow B1, the pushing projection 116 presses down the working shaft 117, thereby pressing down the clamping member 35b against the spring force of the compression coiled spring 37b, and allowing the respective segments 107a and 107b to be released from the radially, inward constrained condition by the clamping member 35b to return radially and outward by the action of the restoring force, and to release the inserted cutting tool 3 from its held state.

Figure 10:
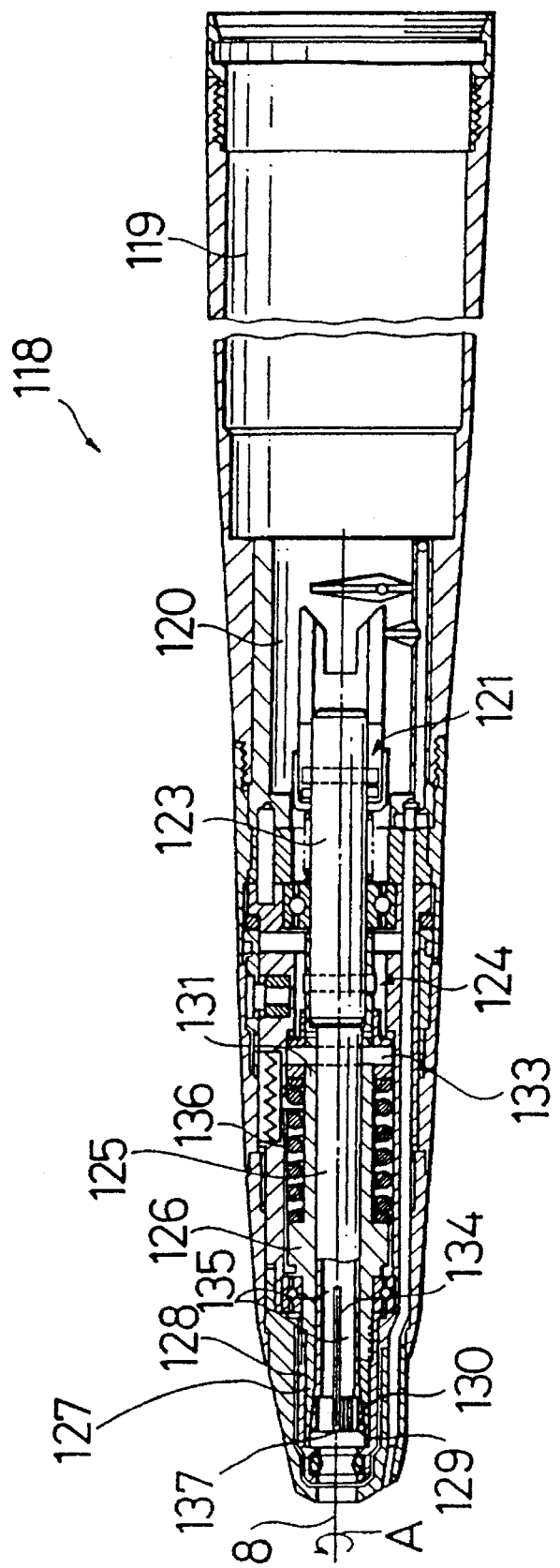
FIG. 10 is a sectional view showing a straight type handpiece 118 according to another embodiment of the present invention.

As another embodiment of the present invention, as is shown in FIG. 10, the present invention may be carried out with a straight type handpiece 118, with advantages. This handpiece 118 is provided with a built-in micro motor 119, and its output shaft 120 is connected with a rotation shaft 123 through a universal coupling 121, and this rotation shaft 123 is connected with a collet chuck 125 and a pressing shaft 126 via a universal coupling 124. At the tip of the pressing shaft 126, a clamping member 127 and a sleeve 128 are provided coaxially. The collet chuck 125, pressing shaft 126, clamping member 127 and sleeve 128 compose a rotor.

On the inner circumference of this clamping member 127, there is formed a truncated cone-like inner circumference 129 widening toward the tip (leftward in FIG. 10). Further, on the outer circumference of the tip of the collet chuck 125 over which the clamping member 127 is mounted, there is formed a truncated cone-like guide surface 130 which faces the inner circumference 129. The collet chuck 125 and the clamping member 127 are connected to each other with a pin 133 both ends of which are fitted in a long pore formed along the axis of the clamping member 127, and the collet chuck 125 may be displaced axially with respect to the clamping member 127.

The tip of the collet chuck 125 is provided with a plurality of axially extending dividing grooves 134 to provide a plurality of segments 135. By forcing the cutting tool 3 into this collet chuck 125, the collet chuck 125 is displaced rightward in FIG. 10, with respect to the pressing shaft 126 and the clamping member 127, and with this displacement the respective protrusion sections 137 of the segments 135 may clamp the outer circumference 60 of the cutting tool 3 with great strength. Upon extraction of the cutting tool 3, the collet chuck 125 which had clamped the cutting tool 3 is displaced leftward in FIG. 10, against the spring force of the compression coiled spring 136, thereby pushing out the respective segments 135 to estrange the respective protrusion sections 37 from the outer circumference of the cutting tool 3, and thus the extraction of the cutting tool 3 is promoted. Also, this straight type handpiece 118 may be formed with a protrusion section 137 according to the present invention to prevent the sliding in the directions of axis and rotation to securely keep the cutting tool 3 held by the collet chuck 125, thereby allowing driving at high-speed rotation without creating vibrations.

In the foregoing embodiments, the working shaft 31 and the clamping member 35 are provided separately in the same manner as the pressing shaft 126 and the clamping member 127, nevertheless, they may be formed integrally with each other according to another embodiment of the present invention.

Figure 11:
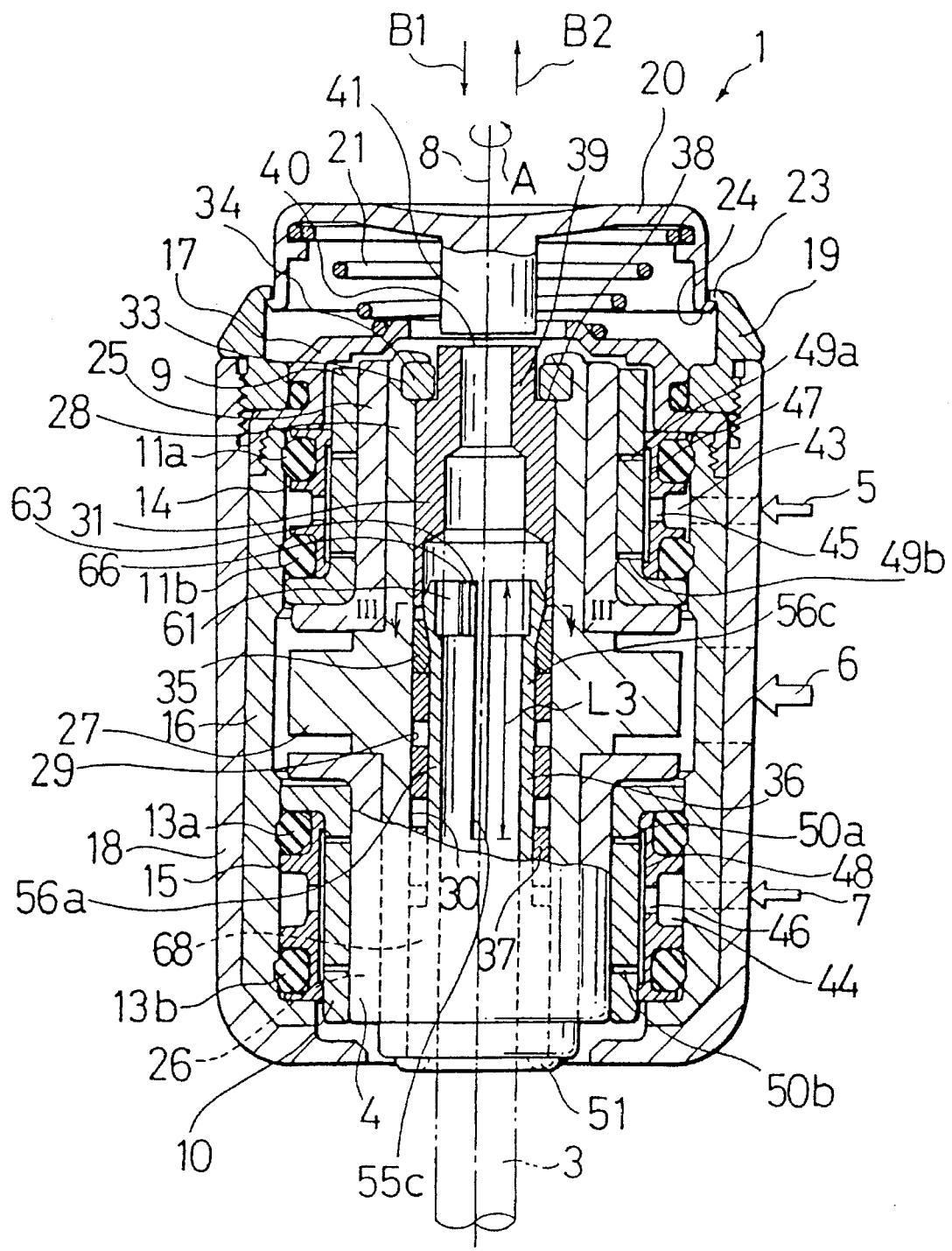
FIG. 11 is a sectional view showing the inner structure of the head 1c of an air turbine handpiece according to another embodiment of the present invention.
Figure 12A:
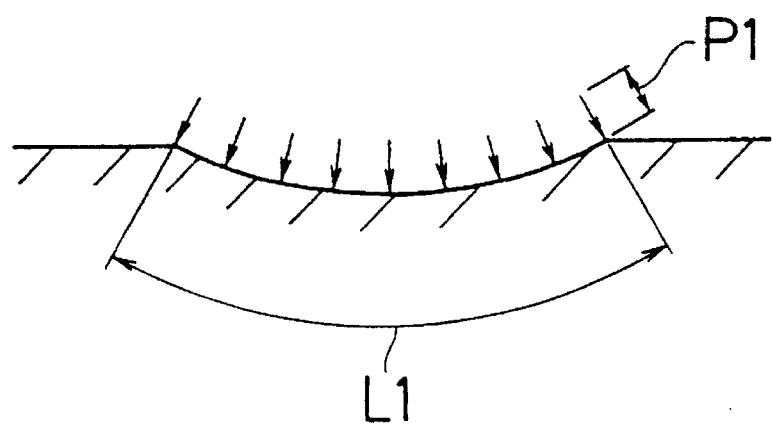
FIGS. 12A, 12B are illustrative views explaining the condition of the force applied to the pushing surface of the manipulation member.
Figure 12B:
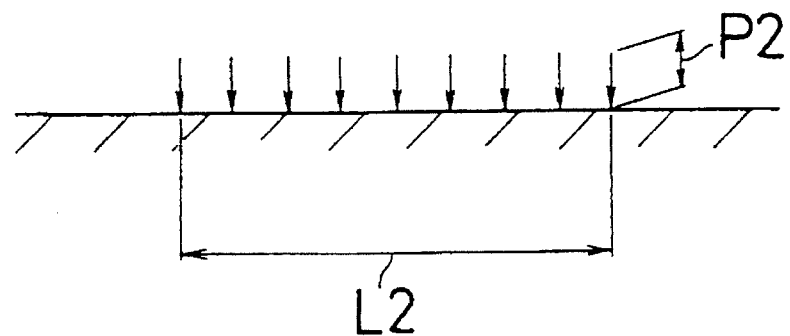

FIG. 11 is a sectional view showing the internal structure of the head 1C of the dental air turbine handpiece according to a further embodiment of the present invention. The head 1C of this embodiment has roughly the same internal structure as the head 1 shown in FIG. 1, and like members are designated by like reference symbols. According to this embodiment the pushing surface 201 of a manipulation member 200 is curvedly formed into a concave. This concave may be pressed down with the finger to push the manipulation member 200 in the direction of the arrow B1, thereby removing the cutting tool. FIG. 12 is a view illustrating the condition of the force applied to the finger in the case where the pushing surface of the manipulation member is a plane or curved into a concave. The area of the pushing surface which may be contacted with the finger is L1 in the case of the concave as shown in FIG. 12(1), and L2 in the case of the plane as shown in FIG. 12(2). Because L1>L2 the force P required for the pressing is $$P = L1 \times P1 = L2 \times P2$$

and thus the forces per unit area-that is, the pressures P1 and P2 on the finger satisfy the relationship: P1<P2 according to the above equation. In other words, when the manipulation member 200 with the concave pushing surface 201 is used, the, finger may press with uniform force over the entire finger, with greater ease than in the case where part of the finger must press harder. The finger used is often the thumb, in which case the radius of curvature of the concave surface is preferred to be 25–35 mm.

Further even with the one of the prior art disclosed in Japanese Unexamined Patent Publication JP-U 56-151035 wherein the whole manipulation member 221 is formed into a concave, and has a bottom 223 or a roughly plane recess 222, since the pushing surface is a plane, part of the finger must press harder for the same reasons as described above. In addition, in the case where the finger is wider than the recess 222, part of the finger comes into contact with the corner.

Figure 13:
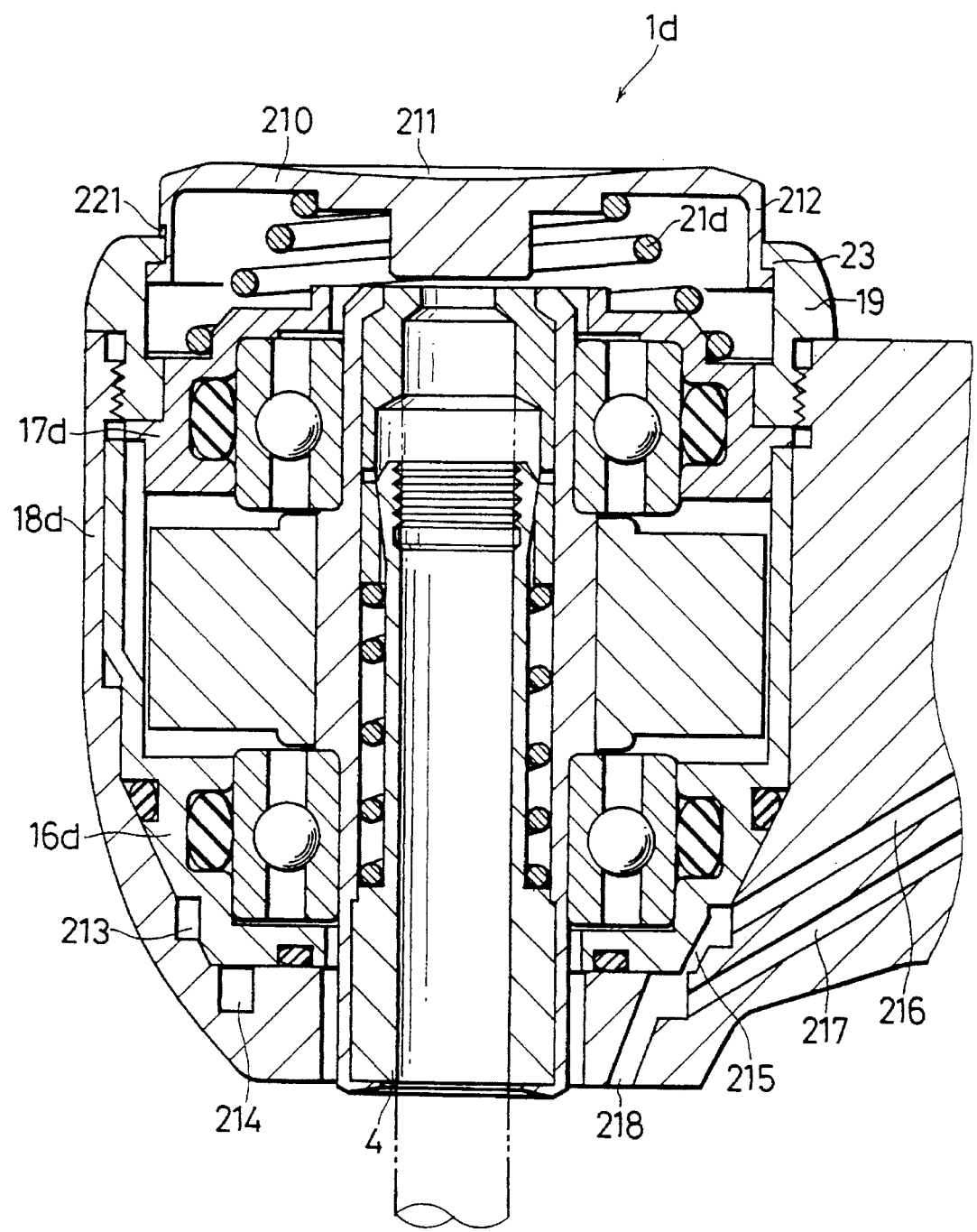
FIG. 13 is a sectional view showing the inner structure of the head 1d of a ball bearing handpiece according to another embodiment of the present invention.
Figure 14:
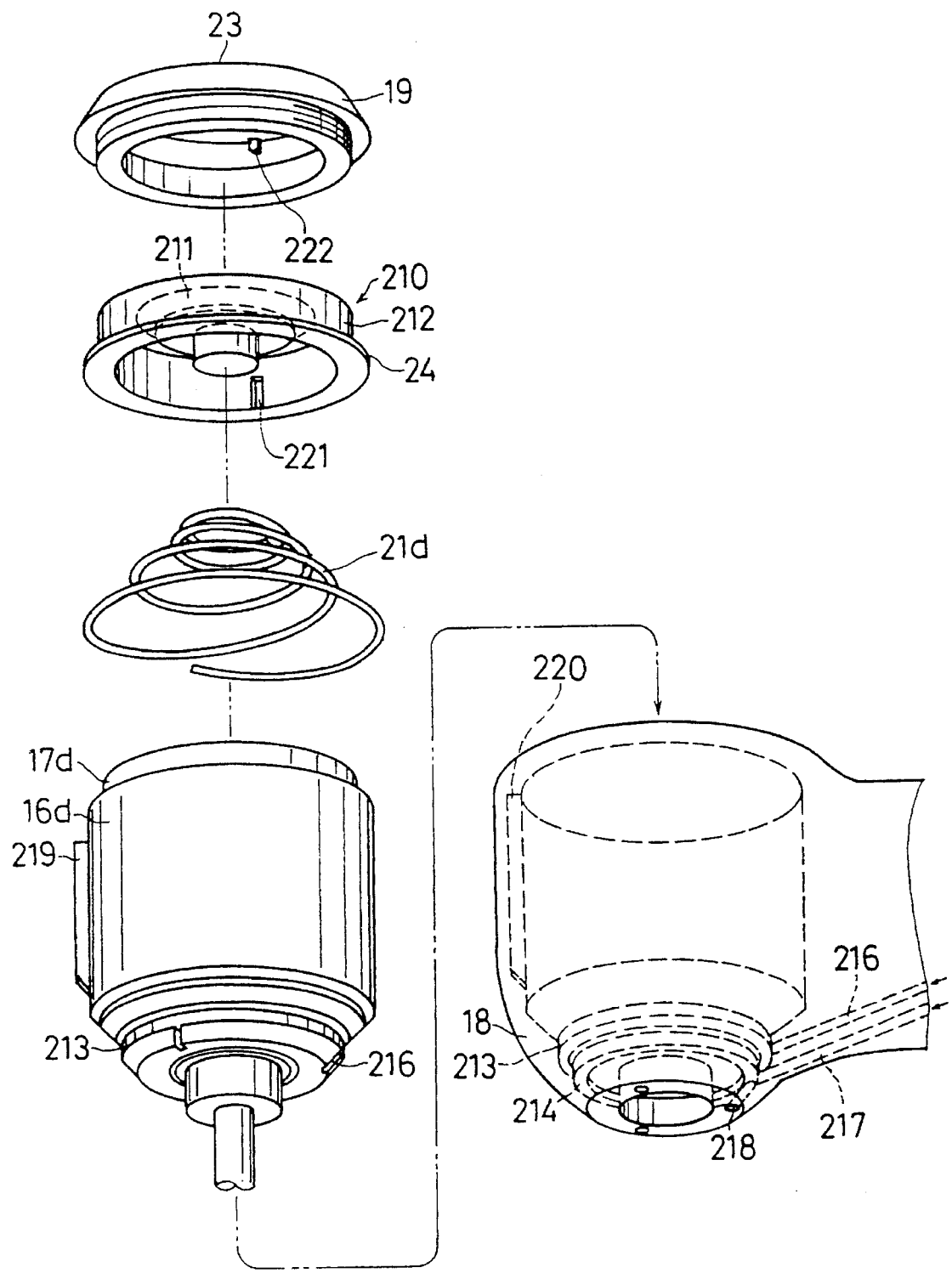
FIG. 14 is an exploded view in perspective of the ball bearing handpiece.
Figure 15:
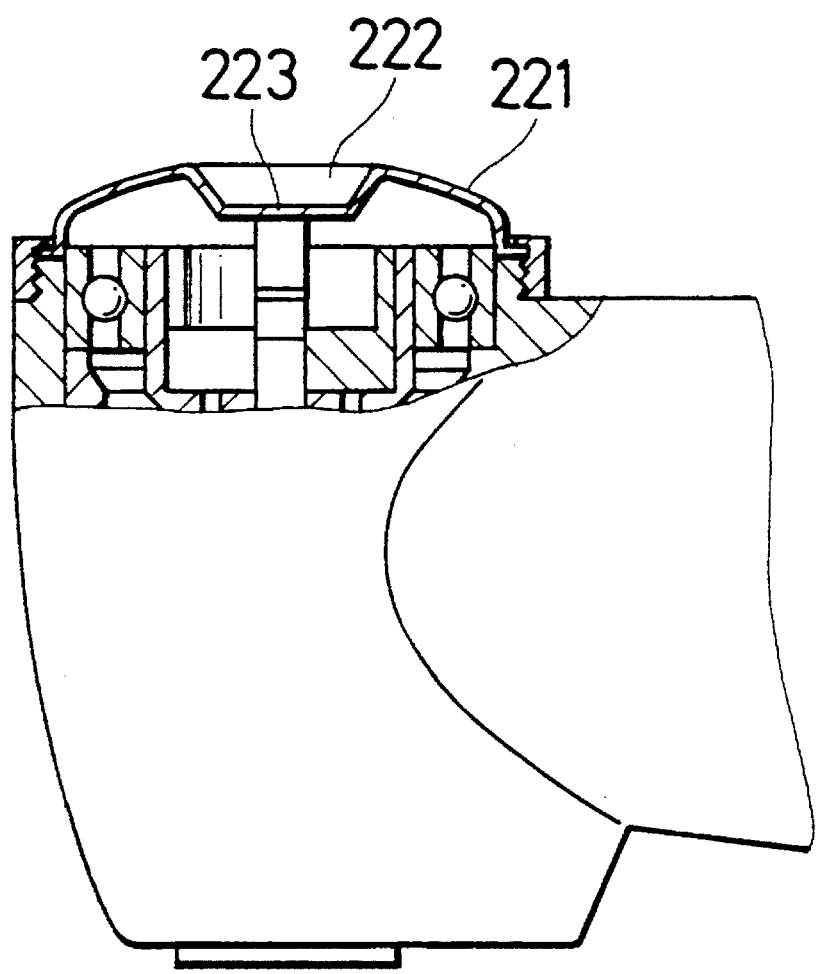
FIG. 15 is a partially cutaway view showing the neighborhood of the manipulation member of a conventional handpiece.

FIG. 13 is a sectional view showing the internal structure of the head 1d of a dental ball bearing handpiece according to another embodiment of the present invention, and FIG. 14 is an exploded, perspective view. The head 1d of the present embodiment has almost the same internal structure as the head 1b shown in FIG. 9; details of the construction of the members are not shown. Also according to the present embodiment, the pushing surface 211 of the manipulation member 210 is curvedly formed into a concave. Deferent from the one shown in FIG. 7, the conic coiled spring 21d widens downward. The side 212 of the manipulation member 210 is pressed against a cover member 19, and a little tapered to keep cuttings out. Furthermore, several slit grooves 221 are provided on the side 212, whereas several protrusion sections 222 which fit in the grooves are provided on inward clampings 23 of the cover member 19. Under the conic coiled spring 21d, there is provided a liner 16d engaged threadedly with a liner cap 17d which is received in a metal head housing 18d. A first annular groove 213 and a second annular groove 214 are formed between the outer circumference of the liner 16d and the inner circumference of the head housing 18d. In the present embodiment, the first annular groove 213 is defined by both the liner 16d and the head housing 18d, while the second annular groove 214 is defined by the inner circumference of the head housing 18d. The two annular grooves are communicated with each other via a plurality of notched grooves 215 arranged on the outer circumference of the liner 16d. The first annular groove 213 and the second annular groove 214 are connected to piping 216 for a first fluid (compressed air), and to piping 217 for a second fluid (water), respectively. By operating a valve (not shown), the compressed air, water or a mixed fluid thereof is gushed out through a fluid jet 218 for cooling treatment of the sites, such as teeth, subjected to cutting. A protrusion 219 arranged on the liner 16d is inserted into a groove 220 arranged in the head housing 18d to secure the liner 16d during rotation of the rotor 4 in the liner 16d.

In the foregoing embodiments, the collet chucks 36, 36a, 36b and 125 provided in the heads 1, 1a, 1b, 1c and 1d according to the present invention serve, due to the existence of the respective protrusion sections 66, 81, 110 and 137, to minimize the contact areas between the outer circumference of the cutting tool 3 and the inner circumferences of the collet chucks 36, 36a, 36b and 125, or the inner circumferences 67 of the respective protrusion sections 66, 81, 110 and 137.

By the displacement of the clamping members 35, 35a, 35b and 127 in the direction of the axis 8 with respect to the collet chucks 36, 36a, 36b and 125, the collet chucks 36, 36a, 36b and 125 press the respective segments 56a, 56b, 56c; 79a, 79b; 107a, 107b; and 175 inward in a radial direction to displace the respective protrusion sections 66, 81, 110 and 137 inward in a radial direction and hold the cutting tool 3.

The collet chucks 36, 36a, 36b and 125, through their displacement in the direction indicated by the arrow B via manipulation with the manipulation members 20, 115, 200 and 210, indirectly displace the clamping members 35, 35a, 35b and 127 in the direction of the axis 8 with respect to the collet chucks 36, 36a, 36b and 125. This displacement releases the respective segments 56a, 56b, 56c; 79a, 79b; 107a, 107b; 175 from the radial, inward pressing force of the clamping members 35, 35a, 35b and 127, resulting in release of the cutting tool 3. Thus, the cutting tool 3 is detached from the collet chucks 36, 36a, 36b and 125.

In order to extract the cutting tool 3 from the collet chucks 36, 36a, 36b and 125, the clamping members 35, 35a, 35b and 127 are displaced in the direction of the axis 8 with respect to the collet chucks 36, 36a, 36b and 125 to release the respective segments 56a, 56b, 56c; 79a, 79b; 107a, 107b; and 175 from the pressing force. The force to be applied to the manipulation members 20, 115, 200 and 210 required for this manipulation depends on the sliding frictional force between the collet chucks 36, 36a, 36b and 125 and the clamping members 35, 35a, 35b and 127.

The sections forming the protrusion sections 66, 81, 110 and 137 and the remaining sections other than the protrusion sections 66, 81, 110 and 137 have different reaction forces to the clamping members 35, 35a, 35b and 127. That is, the remaining sections other than the clamping sections 66, 81, 110 and 137 may displace inward in a radial direction in response to the radial, inward pressing force of the clamping members 35, 35a, 35b and 127 to minimize the reaction force to the clamping members 35, 35a, 35b and 127, whereas, in the case of the sections forming the clamping sections 66, 81, 110 and 137, because of the intervening protrusion sections 66, 81, 110 and 137, the reaction force to the pressing force exerted on the cutting tool 3 is applied to the clamping members 35, 35a, 35b and 127, inward in a radial direction.

In this way, the contact area between the protrusion sections 65, 81, 110 and 137 which clamp and hold the cutting tool 3, and the cutting tool 3 is minimized-that is, the smaller the circumferential lengths of the protrusion sections 66, 81, 110 and 137 are, the smaller the radial, inward force exerted on the clamping members 35, 35a, 35b and 127 becomes, and eventually the sliding friction force between the clamping members 35, 35a, 35b and 127 and the collet chucks 36, 36a, 36b and 125 is minimized.

With this construction, it is possible to operate the manipulation members 20, 115, 200 and 210 with a small force to displace the clamping members 35, 35a, 35b and 127 in the direction of the axis 8 with respect to the collet chucks 36, 36a, 36b and 125, thereby releasing the respective segments 56a, 56b, 56c; 79a, 79b; 107a, 107b; and 175 from their radial, inward constrained conditions to extract the cutting tool 3.

The cutting tool 3 held by these collet chucks 36, 36a, 36b and 125 usually has a Vickers' hardness $H_v$ on the order of 200–400, but sometimes has a Vickers' hardness $H_v$ of 700–800. In such cases where a harder cutting tool 3 is used, however, due to the lower hardness of the collet chucks 36, 36a, 36b and 125 than the cutting tool 3, the respective protrusion sections 66, 81, 110 and 137 tend to wear away, and accordingly there is a risk of degrading the performance of the collet chucks 36, 36a, 36b and 125 to hold the cutting tool 3, including eccentric holding of the cutting tool 3 with respect to the axis 8. Therefore, the respective protrusion sections 66, 81, 110 and 137 of the collet chucks 36, 36a, 36b and 125 must have a Vickers' hardness of 800 or more. In order to provide them with such high hardness, the entire collet chucks 36, 36a, 36b and 125 may be formed from a high hardness material, for example, a WC (tungsten carbide) cemented carbide.

In cases where all of the collet chucks 36, 36a, 36b and 125 are formed from a high hardness material such as cemented carbide, however, cracks and cuts tend to be formed due to poor toughness, or high brittleness. In addition, high hardness materials are expensive, and are thus costly to obtain, and also have poor workability, meaning difficulties and much time and effort required for working, which factors eventually increase working cost. In order to solve these problems, the present invention presents a construction such that the respective protrusion sections 66, 81, 110 and 137 of the collet chucks 36, 36a, 36b and 125 have high hardness for its internal surface layer, for example to a depth of around 10–30 μm from the surface. Thus, the surface with increased hardness prevents wearing of the respective clamping sections 66, 81, 110 and 137, and the internal toughness prevents the formation of cracks and cuts.

Methods of improving the hardness of the surface layer include, for example, gas nitriding treatment wherein steel to be worked into collet chucks 36, 36a, 36b and 125 is heated in an atmosphere of ammonia gas at 475°–580° for 20–100 hours to decompose the ammonia gas to separate nitrogen, and the nitrogen is diffused and penetrates into the steel to nitride components contained in the steel, e.g., aluminum, chromium, vanadium and molybdenum, and the resulting strain hardness hardens the surface layer of the steel.

Other methods include gas soft nitriding treatment at a somewhat higher treatment temperature than the gas nitriding treatment, and plasma nitriding treatment wherein plasma energy promotes the nitriding. Nitriding treatments such as gas nitriding treatment, gas soft nitriding treatment and plasma nitriding treatment, etc. may be carried out after treatments for quenching, drawing, etc., and after measurement to prescribed dimensions.

Yet another method is carburization treatment wherein carbon is diffused and penetrated into the surface of the steel, and after penetration the surface is hardened by quenching.

In addition to the foregoing methods, coating treatment with TiN (titanium nitride) or TiCr (titanium-chromium alloy), Tuftride process, WC flame spraying, vacuum diffusion treatment, etc. as well. These are enumerated only as examples, and other methods may be used.

The present invention may be carried out in various other manners without departing from the spirit and essential characteristics thereof. Therefore, the foregoing embodiments are only illustrative in any aspect, and the scope of the present invention is determined solely by the appended claims, without bound by the main body of the specification.

Further, all changes and modifications that fall within equivalence of the appended claims are within the scope of the claims.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A dental cutting tool holder comprising:

a collet chuck into which a dental cutting tool is inserted detachably, and which comprises a right cylindrical section and a plurality of arc-section segments which are contiguous to the cylindrical section and divided in a circumferential direction;

a rotor into which the collet chuck is inserted, and which is driven for rotation around the axis of rotation together with the collet chuck; and a clamping member which intervenes between the collet chuck and the rotor to press the respective segments inward in a radial direction by the displacement thereof toward one axial end relative to the collet chuck while releasing the inward, radially pressed condition by the displacement thereof toward an other axial end, wherein the respective segments are formed with a recess section located back from the outer circumference of the inserted cutting tool outward in a radial direction, and an axial protrusion section jutting out inward in a radial direction from an inner circumference of the recess section.

2. The dental cutting tool holder as claimed in claim 1, wherein the respective protrusion sections form the respective segments at their upstream ends in the direction of rotation of the rotor.

3. The dental cutting tool holder as claimed in claim 1 or 2, wherein each protrusion section is provided with a plurality of notches spaced apart along the axis of the collet chuck.

4. A dental cutting tool holder comprising:

a collet chuck into which a dental cutting tool is inserted detachably, and which comprises a right cylindrical section and a plurality of arc-section segments which are contiguous to the cylindrical section and divided in a circumferential direction;

a rotor into which the collet chuck is inserted, and is driven for rotation around the axis of rotation together with the collet chuck;

a clamping member which intervenes between the collet chuck and the rotor to press the respective segments inward in a radial direction by the displacement thereof toward one axial end relative to the collet chuck while releasing the inward, radially pressed condition by the displacement thereof toward an other axial end;

a hollow cylindrical head housing for receiving the collet chuck, rotor and clamping member; and a manipulation member which is provided at the other axial end of the head housing and which releases the dental cutting tool upon axial pressing with the finger, wherein a pushing surface of the manipulation member is curvedly formed into a concave.

5. The dental cutting tool holder as claimed in claim 4, wherein the head housing is formed with first and second annular recess grooves which are open to the facing internal space and communicated with each other, and an aperture in either of the first and second annular recess grooves positioned closer to the bottom of the head housing, which inclines inward in a radial direction toward the tip of the cutting tool, and injects first and second fluids which are separately supplied to the first and second annular recess grooves, or a mixture thereof.

* * * * *